(12) United States Patent
Gilman

(10) Patent No.: US 6,599,309 B1
(45) Date of Patent: Jul. 29, 2003

(54) PIN-LESS SURGICAL INSTRUMENT (75) Inventor: Brian W. Gilman, Halifax, MA (US)

(73) Assignee: TNCO, Inc., Whitman, MA (US)

( * ) Notice: Subject to any disclaimer, the term of this patent is extended or adjusted under 35 U.S.C. 154(b) by 116 days.

(21) Appl. No.: 09/642,822

(22) Filed: Aug. 22, 2000

Related U.S. Application Data (60) Provisional application No. 60/152,939, filed on Sep. 9, 1999.

(51) Int. Cl.[7] .............................................. A61B 17/44
(52) U.S. Cl. ...................................................... 606/205
(58) Field of Search ................................. 606/207, 206, 606/174, 184, 51, 157, 208, 170, 52, 209, 210, 211, 83, 167, 22, 205

(56) References Cited

U.S. PATENT DOCUMENTS

| | | | | |
|---|---|---|---|---|
| 1,754,806 A | * | 4/1930 | Stevenson | 128/321 |
| 4,369,788 A | * | 1/1983 | Goald | 128/321 |
| 4,644,951 A | * | 2/1987 | Bays | 128/305 |
| 4,712,545 A | * | 12/1987 | Honkanen | 128/305 |
| 4,957,500 A | * | 9/1990 | Liang et al. | 606/157 |
| 5,152,780 A | * | 10/1992 | Honkanen et al. | 606/205 |
| 5,395,375 A | * | 3/1995 | Turkel et al. | 606/83 |
| 5,423,854 A | * | 6/1995 | Martin et al. | 606/205 |
| 5,431,674 A | * | 7/1995 | Basile et al. | 606/170 |
| 5,601,578 A | * | 2/1997 | Murphy | 606/148 |
| 5,603,724 A | * | 2/1997 | O'Connor | 606/207 |
| 5,643,307 A | * | 7/1997 | Turkel et al. | 606/184 |
| 5,868,786 A | * | 2/1999 | DiFrancesco | 606/208 |
| 5,906,630 A | * | 5/1999 | Anderhub et al. | 606/205 |
| 5,908,420 A | * | 6/1999 | Parins et al. | 606/51 |
| 6,019,780 A | * | 2/2000 | Lombardo et al. | 606/207 |

* cited by examiner

Primary Examiner—John J. Calvert
Assistant Examiner—Alissa L Hoey
(74) Attorney, Agent, or Firm—John S. Hale; Gipple & Hale (57) ABSTRACT A miniature articulated tip instrument for surgical and like uses, comprising: a thumb housing with an elongated fixed jaw assembly mounted thereto and extending therefrom. A movable jaw actuator member is slidably mounted in a groove formed in the said fixed jaw assembly, the proximal end of the actuator member being seated in a finger housing which is mounted to and spring biased from the thumb housing. A movable jaw defining at least one arcuate projection extending therefrom for pivotal engagement with the actuator member is additionally provided with a second arcuate projection and a concnetric cutout on its opposite side from the second arcuate projection to engage the fixed jaw member and provide a pivot point. The actuator member drives the movable jaw member in a pivoting motion within a throughgoing slot formed in the fixed jaw member within a range of movement with respect to the fixed jaw assembly between extended and retracted positions for effecting selective user controlled working movement.

17 Claims, 10 Drawing Sheets

PIN-LESS SURGICAL INSTRUMENT

This application claims benefit of U.S. Provisional application serial No. 60/152,939, filed Sep. 9, 1999.

BACKGROUND OF THE INVENTION

The present invention is generally directed to microinstrumentation in the nature of articulating hand held instruments used in micro-surgery, electronic microassembly and similar applications of grasping, cutting, punching out, probing and like usages.

Recent developments of miniaturized and other surgical endoscopic instruments have encountered structural limits as the cross-sections become reduced in size. As the tip size of such instruments is reduced, the likelihood of breakage and/or the need to reduce applied force is increased. The high strength and toughness of improved metal alloys have not overcome this problem.

In the typical surgical punch, the two jaw members are adapted to be alternatively opened and closed relative to one another by manipulation of a scissor type handle. These conventional surgical punches utilize an inefficient mechanical design in which the pivot points of the jaws of the punch are subjected to significant stress during use thus shortening the life of the surgical punch. The stress factor is multiplied due to the fact that conventional surgical punches typically use tiny pivot pins to hinge the two jaw members together. Such pivot pins are susceptible to breakage during use, rendering the surgical punches inoperable or worse and result in tiny fragments of sheared metal being deposited in the surgical area. Any number of attempts have been made to solve this breakage problem by increasing the dimensions of selected parts of the surgical punches so as to increase part strength and by attempting to product surgical punches which do not use pivot points. Likewise conventional surgical forceps have the same limitation as surgical punches, e.g. excessive stress at the jaws pivot point leading to early failure or excessive size which hampers their use in micro surgery.

DESCRIPTION OF THE PRIOR ART

The present invention is directed toward a pin-less pivotable surgical instrument which overcomes the pin shearing problems noted above. A pin-less surgical instrument for knee arthroscopy is disclosed in U.S. Pat. No. 4,712,545. In this instrument the pin type pivot point has been replaced by a moveable jaw member attached to the stationary jaw member by an arcuate lug and groove assembly allowing pivotal movement of the moveable jaw member about an imaginary central axis of the arcuate grooves between an open and closed position. The moveable jaw member is attached to a coupling member so that when the coupling member is moved linearly in a first direction relative to the first stationary jaw member, the second movable jaw member will open away from the first stationary jaw member and when the coupling member is moved linearly in a second opposite direction relative to the first stationary jaw member, the second movable jaw member will close towards the first stationary jaw member.

Another pin-less instrument in the nature of a colposcopic biopsy punch with removable sample basket is shown in U.S. Pat. No. 5,643,307. In this disclosure, a stationary jaw in the form of a die having an open top and bottom is coupled to the distal end of the tube and a movable jaw in the form of a punch is pivotally coupled to the stationary jaw by a tongue and groove arrangement. The punch includes a hollow tube and a push rod which extends through the tube, the proximal end of the push rod being coupled to a lever which is pivotally coupled to the handle. Movement of the lever relative to the handle imparts a reciprocal axial movement to the rod relative to the tube. A stationary jaw is coupled to the distal end of the tube and a movable jaw is coupled to the distal end of the push rod. The movable jaw has a pair of arcuate grooves and the stationary jaw has a pair of arcuate flanges which engage the grooves on the movable jaw. The stationary jaw has an upper opening and a lower opening. The movable jaw is therefore movable into and out of the upper opening of the stationary jaw by action of the lever. The movable jaw has cutting teeth which coact with the inner surface of the upper opening of the stationary jaw when the movable jaw is moved from the open position to the closed position.

Typical pin type pivot instruments are shown by U.S. Pat. Nos. 5,906,630 and 5,603,724. In the '724 patent an articulating handle of scissors grip construction has an elongated probe extending therefrom with an elongated actuating linkage portion and a tip portion at the probe end distal from the handle. The actuating linkage is a shaft fixedly mounted from the handle, with a longitudinal groove or hole receiving an actuating rod and a tip portion at the distal end of the shaft. The tip portion comprises an assembly of relatively moveable components defined as an inner tip and an outer tip. The inner tip moves while the outer tip is stationary. The tip assembly is operated to excise tissue into pieces and has a pivotal mounting with a fixed shaft extension of the outer tip integrally. The actuating linkage extends from an actuating system in the handle through an elongated channel of the probe and terminates in a connection at the inner tip offset from the pivotal mount to provide a levering articulation motion to the inner tip between upper and lower positions.

Another device using a pivot lug and a rotatable jaw with a pivot seat which wraps around the lug in normal operation is disclosed in U.S. Pat. No. 5,868,786. U.S. Pat. No. 5,908,420 discloses a surgical scissors instrument having a rivet or a screw joining the blade elements.

A tube clamp with a transverse arcuate ridge formed on a stationary member provides a cam for the cam engaging surface of a movable jaw member as is shown in U.S. Pat. No. 4,957,500.

SUMMARY OF THE INVENTION

The present pin-less surgical instrument is constructed using cylinders lying in the same plane as fulcrums for the outer tip/inner tip actuator interaction. The actuator has a hollow semi-cylindrical protrusion which mates to a semi-cylindrical recess formed in an inner jaw. A semi-cylindrical protrusion on the inner jaw is positioned concentric to a recess formed in the inner jaw which captures the actuator in a plane perpendicular to their axes. The inner jaw is provided with two centers, one is the center of fulcrum that is mated to the actuator and the other is the pivot, which is mated to the outer jaw. The inner jaw pivot has one protrusion and one recess at this pivot, concentric to each other of conic or cylindrical design. The protrusion on the inner movable jaw pivot is mated with a complementary form in the outer fixed jaw, keeping the inner pivot captured in one direction. The recess of the inner pivot is also mated with a complementary form in the outer jaw, capturing the inner jaw on a radial plane. The surfaces extend radially, perpendicular to the outer jaw and the inner jaw axes to captivate the inner jaw in two directions. The inner jaw/actuator orbits the pivot as the actuator is moved fore and aft by moving the spring biased finger housing against the thumb housing. This movable inner jaw/fixed outer jaw mechanism may be used as a punch, scissor, or grasper, or any other kind of instrument.

The present inventive instrument can be employed in connection with a number of uses for removing, grasping or cutting tissued specimens internally and externally in a medical context.

It is therefore an object of the invention to provide a surgical instrument for internally cutting, grasping, and/or removing tissue, the instrument having movable jaws.

It is an object of the present invention to produce a surgical instrument which is extremely durable and able have jaws which can withstand significant stress during use without failing.

It is another object of the invention to produce a surgical punch which utilizes a novel pivot so as to minimize the stress on its pivot points during use and which does not employ pivot pins in its construction.

It is a further object to produce a surgical instrument which is small in size and able to work well in confined spaces.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

DESCRIPTION OF THE INVENTION

The preferred mode and best embodiment of the invention is shown in FIGS. 1 through 5, 10, 11 and 17 through 20.

The pin-less surgical instrument 30 is constructed with a thumb housing 32 having a thumb loop 33. The thumb housing 32 is the receptacle for the fixed outer shaft 40 and fixed jaw member 42 which is secured to the thumb housing to preclude movement. The fixed outer shaft 40 and thumb housing 32 may be created as one unit or as an assembly as is presently shown. The moveable finger housing 34 is spring-mounted at 36 to the thumb housing to constantly urge the base or finger loop 35 of the finger housing 34 forward against the biasing action of the coil spring. The spring mounting of thumb and finger housings is well known in the art. The finger housing is joined or mounted with the thumb housing at a single point (fulcrum) as is common in the industry and well known in the art. The finger of the user is the means by which rearward thrust is applied to the finger loop 35 of the finger housing 34 to drive the actuator bar member 50 forward. The fixed jaw member 40 is mounted in the thumb housing 32 and an actuator member 50 is mounted in a groove 49 cut into the fixed jaw member and is slidably mounted thereon. The end 52 of the actuator member is seated in a seat 33 cut into the finger housing thus converting the rotational movement and force of the finger rotating against the thumb into linear movement. This movement is reconverted to rotational movement of the moveable jaw 60 with respect to the actuator bar member 50 at the distance away from the handle. The moveable jaw 60 is rotatably mounted on the tip of the fixed jaw member and is engaged and rotated upward by the camming action of the tip 54 of the actuator arm 50. The actuator arm consists of an elongated member having a rear projection 52 which sits in seat 33 of the finger housing 34, a body 53, a tip 54 constructed with an arcuate cutout 56 forming an arcuate wall 57, an offset arcuate step cutout 58 and a slide guide 59. The arcuate cutout 56 is best seen in FIGS. 3–5 and FIGS. 10–12. The terms moveable jaw and inner tip and fixed jaw member and outer tip are used interchangeably throughout the description. It should also be noted that the moveable jaw can refer to a clamp, forceps or cutter.

Figure 1:
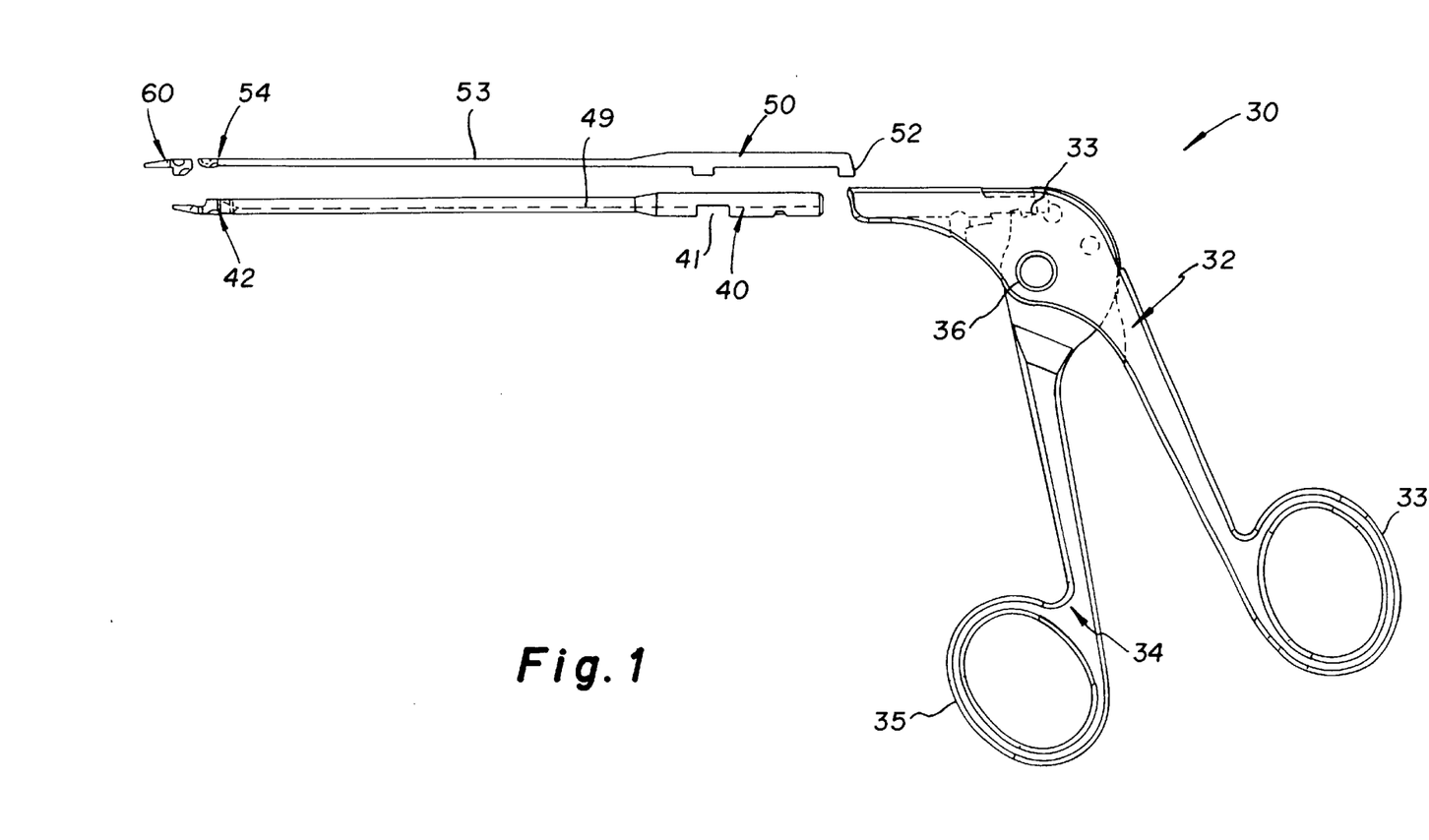
FIG. 1 is a side elevation exploded view of the pin-less surgical instrument.
Figure 2:
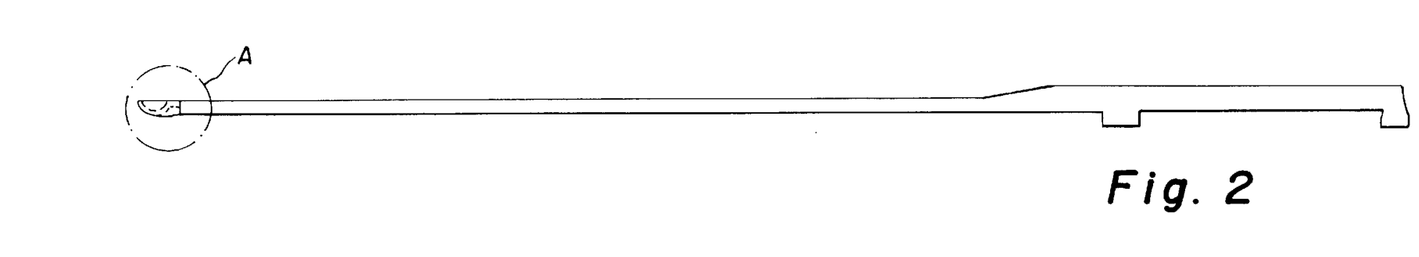
FIG. 2 is an enlarged side elevation view of the actuator bar of the instrument of FIG. 1.
Figure 3:
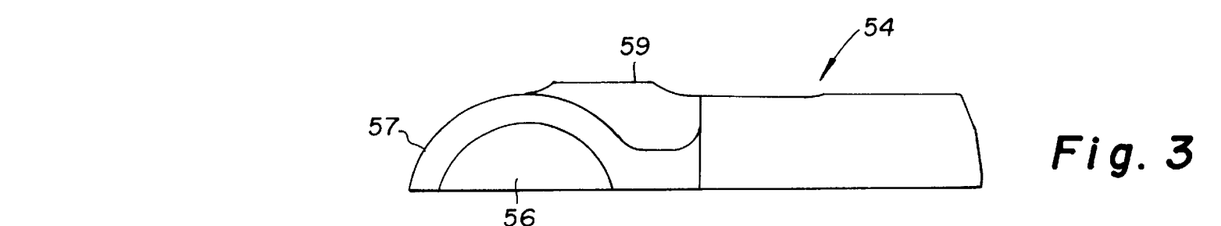
FIG. 3 is an enlarged rear-side inverted view of the tip of the actuator bar of FIG. 2 shown in circle A.
Figure 4:
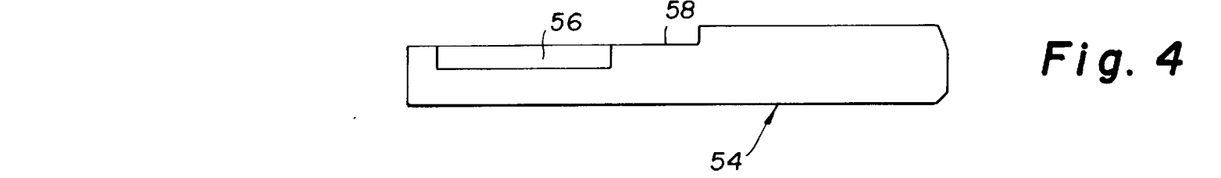
FIG. 4 is an enlarged plan view of the tip of the actuator bar of FIG. 2 shown in circle A.
Figure 5:
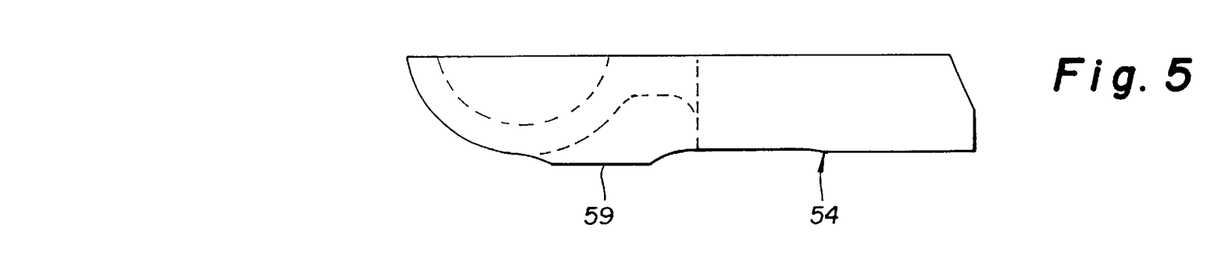
FIG. 5 is an enlarged side elevation view of the tip of the actuator bar of FIG. 2 shown in circle A.
Figures 6, 7:
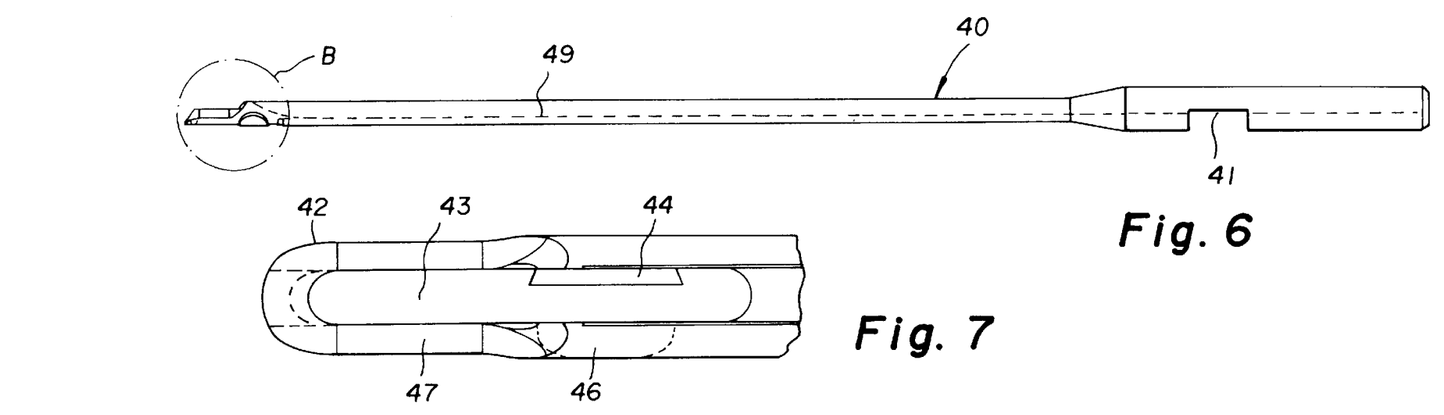
FIG. 6 is an enlarged side view of the fixed jaw member of the instrument of FIG. 1.
FIG. 7 is an enlarged top plan view of the tip section of the fixed jaw member of FIG. 6 shown in circle B.
Figure 8:
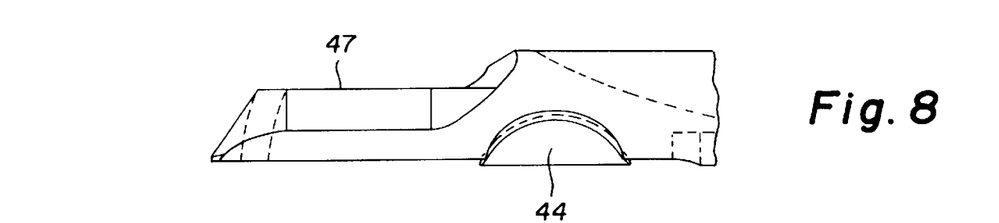
FIG. 8 is an enlarged side elevational view of the tip section of the fixed jaw member of FIG. 6 shown in circle B.
Figure 9:
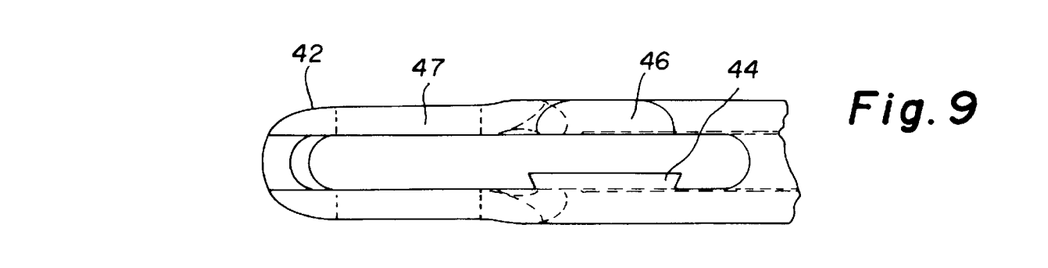
FIG. 9 is a bottom plan rear view of the tip section of the fixed jaw member of FIG. 6 shown in circle B.
Figure 10:
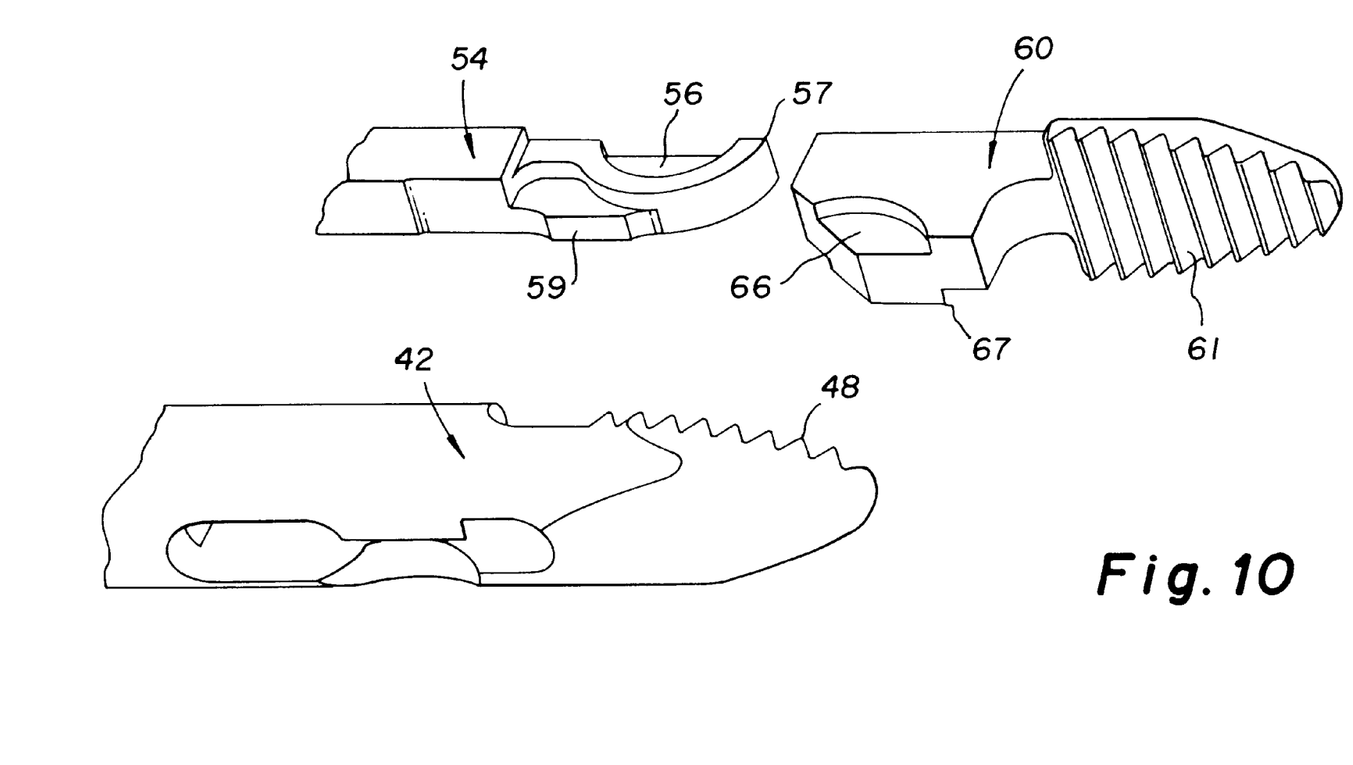
FIG. 10 is a perspective exploded view of the tip end of the fixed jaw member, the actuator bar tip, and the moveable jaw member.

The fixed jaw member 40 is fixedly mounted by pin means (not shown) in a bore cut into thumb member 32 or is constructed of a single construction. The fixed jaw member as noted has a guide groove 49 and defines a cutout 41. An end tip 42 shown in FIGS. 7 through 9 located at the distal end of the fixed jaw member 40 receives moveable jaw 60 as shown in FIGS. 10–12, 17–19 or 21–23. The end tip 42 defines a throughgoing slot 43, an arcuate frustum shaped projection 44 which projects into slot 43, and a throughgoing arcuate cavity 46. The arcuate projection 44 which extends inward into the slot 43 is preferably a frustum conical shape. FIG. 8 shows the arcuate projection 44 as seen through the cavity 46 of the fixed jaw member. The fixed jaw member can be provided with a planar top surface 47 as shown in FIGS. 6–9, 12–14 and 21–24 or sawtooth jaws 48 as shown in FIGS. 10, 11 and 17–20.

Figure 11:
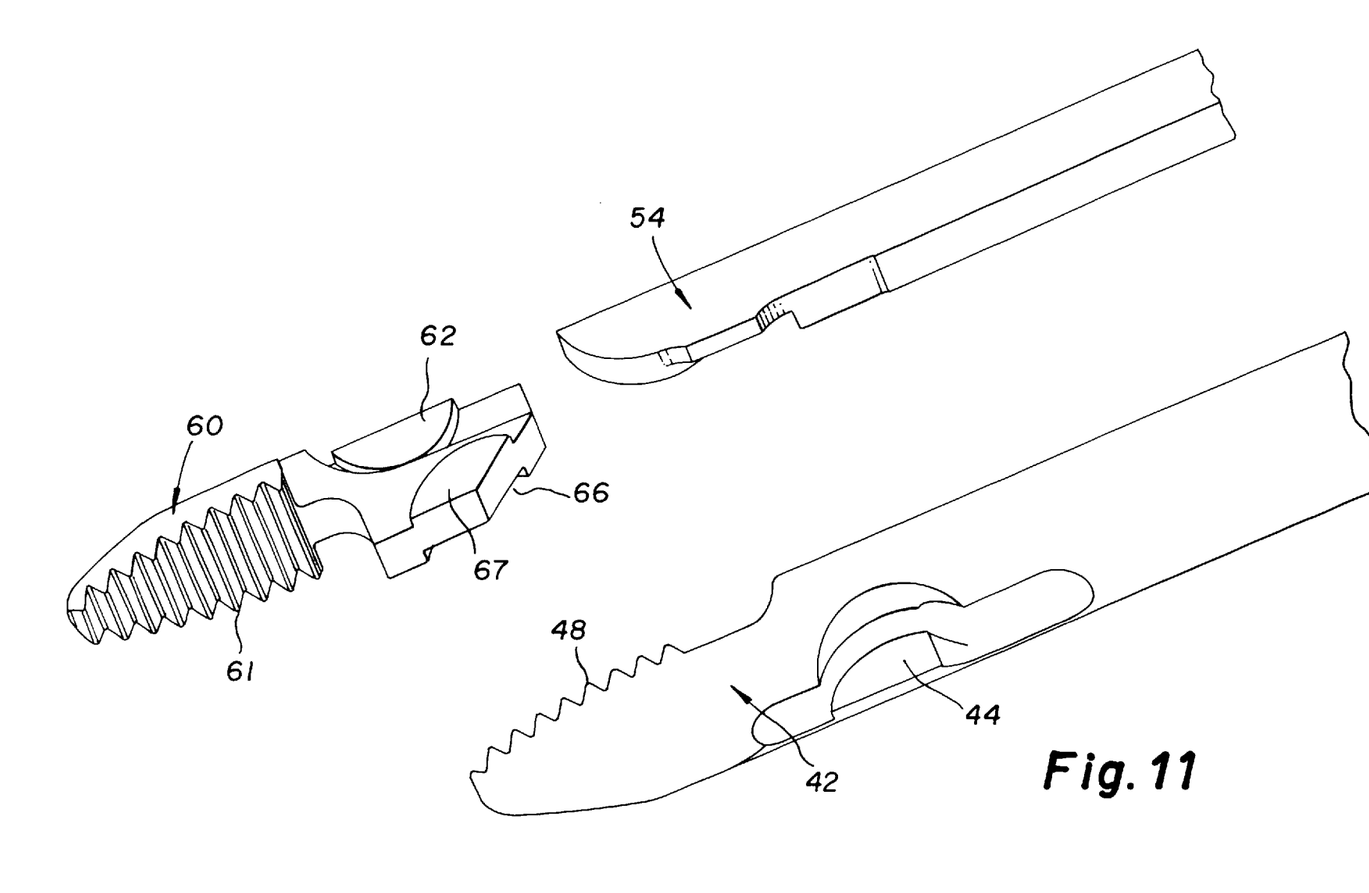
FIG. 11 is a reverse perspective exploded view of the tip end of the fixed jaw member, the actuator bar tip, and the moveable jaw member seen in FIG. 10.
Figure 12:
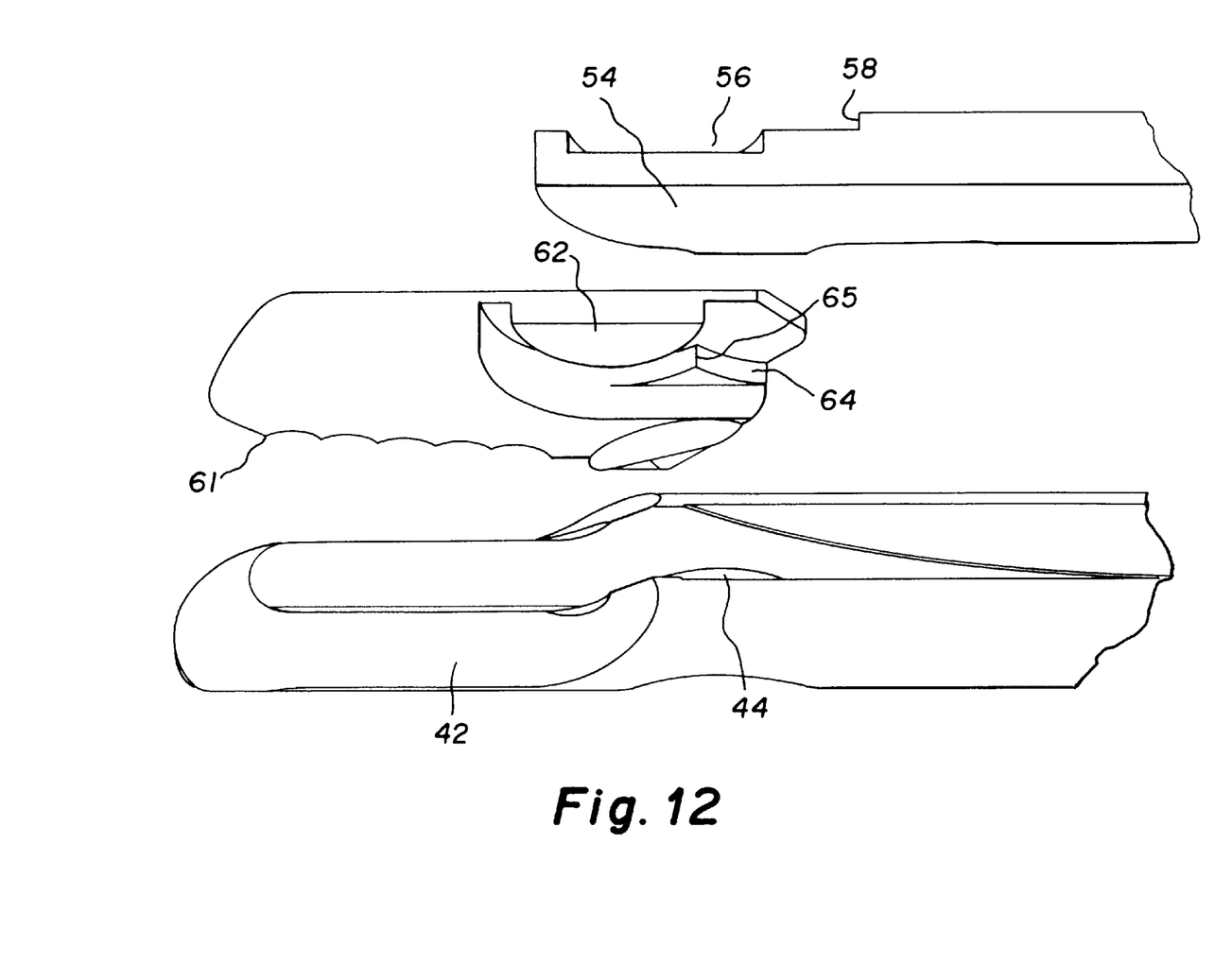
FIG. 12 is another exploded perspective view of a modified embodiment of the tip end of the fixed jaw member, the actuator bar tip, and the moveable cutter jaw.
Figure 13:
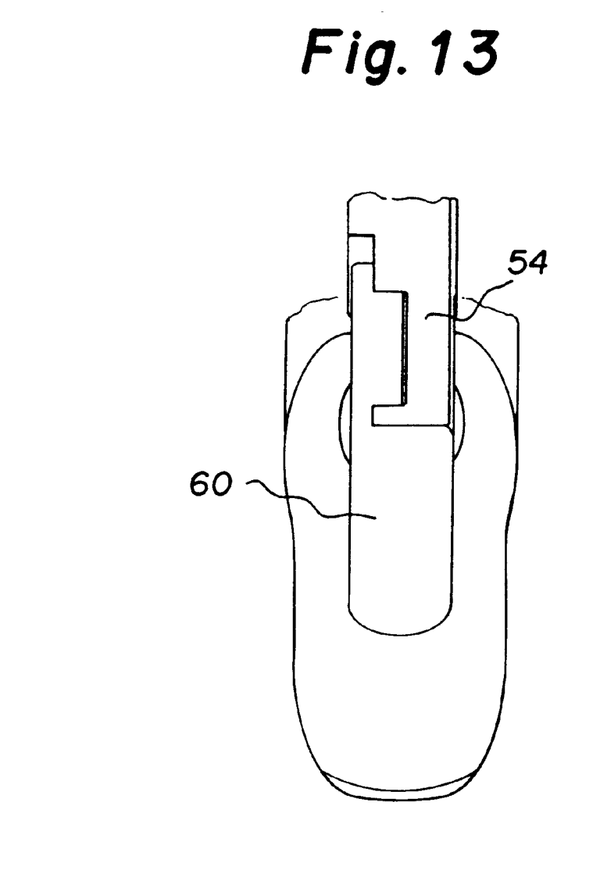
FIG. 13 is an enlarged top plan tip segment showing engagement of the fixed jaw member, actuator member tip and moveable jaw of FIG. 12.
Figure 14:
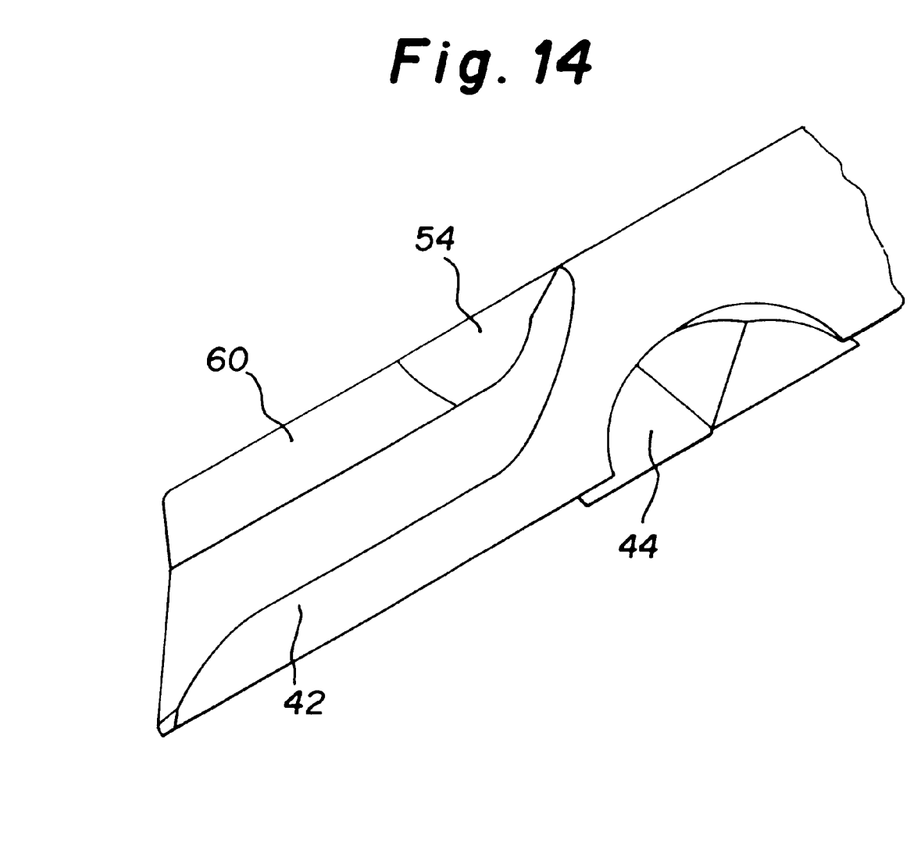
FIG. 14 is a side elevation view of the moveable jaw, actuator arm, and fixed jaw assembly.
Figure 15:
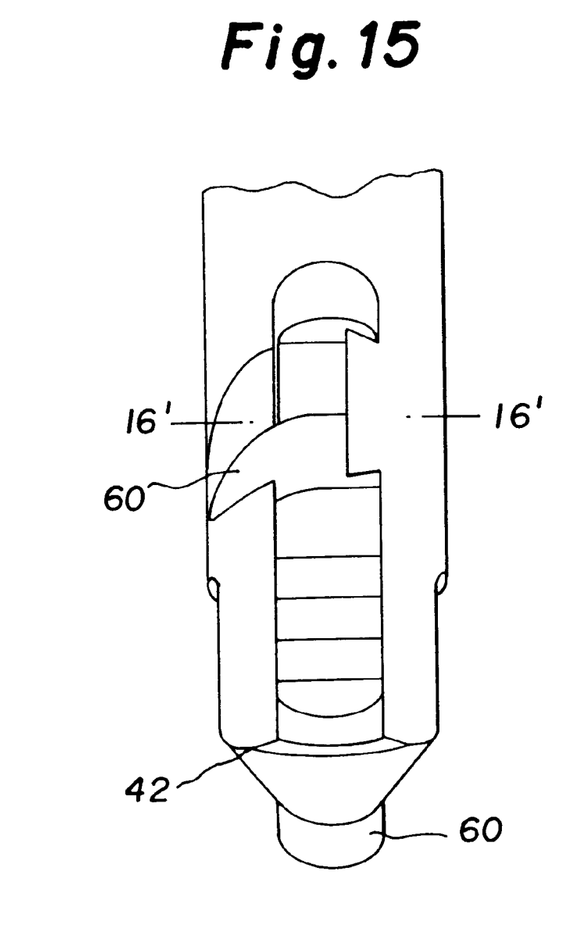
FIG. 15 is an enlarged top plan view of the assembled moveable jaw, actuator arm, and fixed jaw member.
Figure 16:
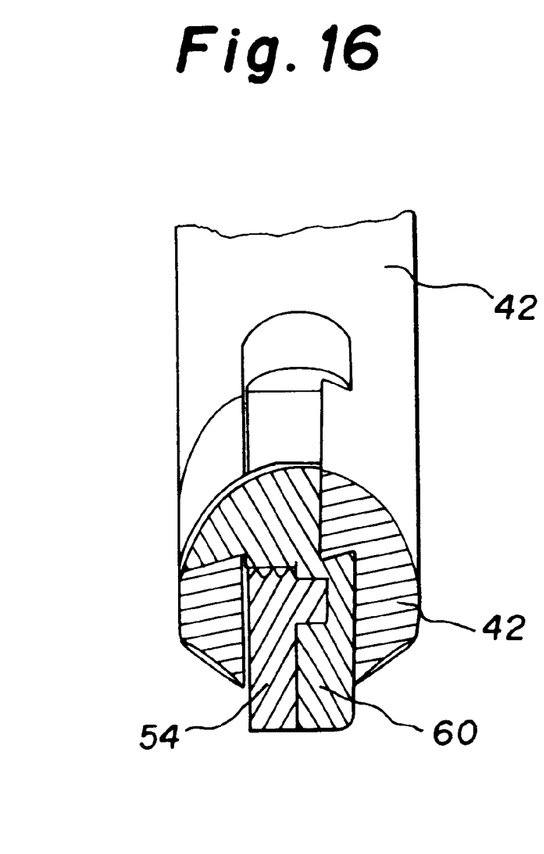
FIG. 16 is a cross section taken along the lines 16'—16' of FIG. 15.
Figure 17:
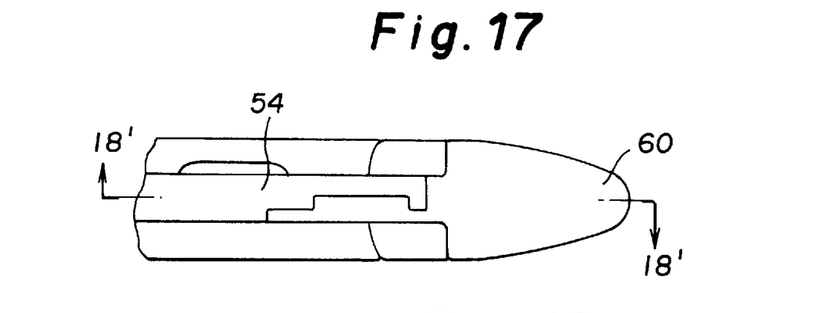
FIG. 17 is an enlarged top plan view of the actuator bar, fixed jaw, and moveable jaw in a closed position.
Figures 18, 19:
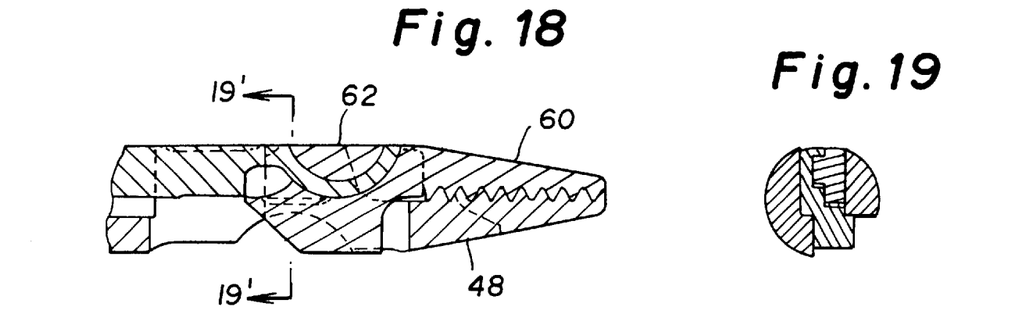
FIG. 18 is a cross section of FIG. 17 taken along the lines 18'—18'.
FIG. 19 is a cross section of FIG. 18 taken along the lines 19'—19' of FIG. 18.
Figure 20:
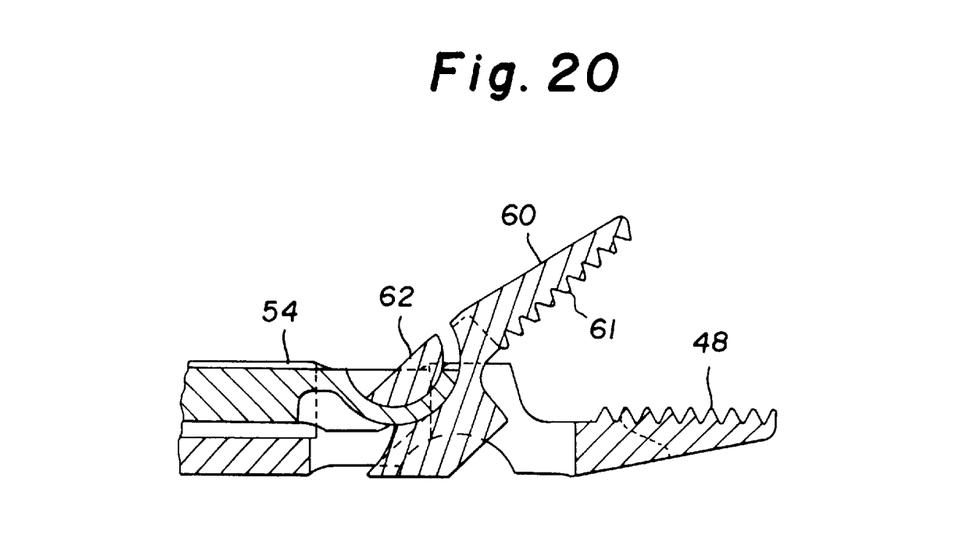
FIG. 20 is a sequential view of FIG. 18 showing the jaws in an open position.
Figure 21:
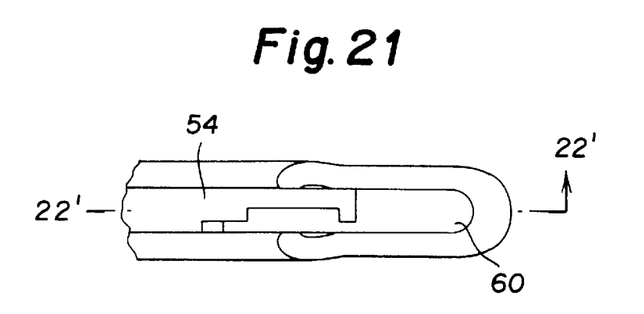
FIG. 21 is a top plan view of another embodiment of the invention.
Figure 22:
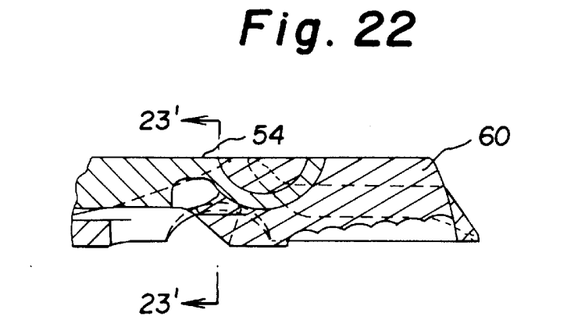
FIG. 22 is a cross section of FIG. 21 taken along the lines 22'—22' of FIG. 21.
Figure 23:
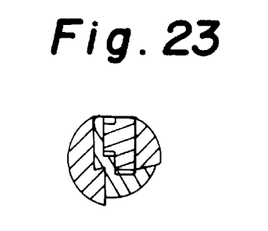
FIG. 23 is a cross section of FIG. 22 taken along the lines 23'—23' of FIG. 22.
Figure 24:
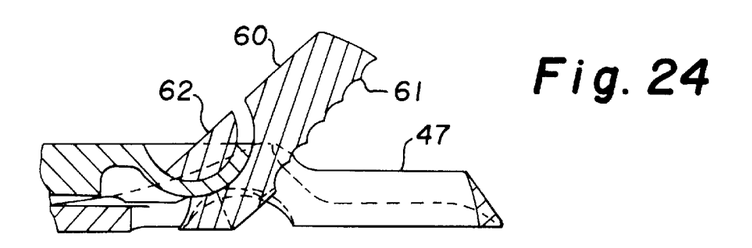
FIG. 24 is a sequential view of FIG. 22 taken showing the jaws in an open position.

The moveable jaw member 60 has a serrated edge 61 (See FIG. 12) for cutting or gripping depending upon the particular desired use and is provided with a hemispherical or arcuate projection 62 which is best shown in FIG. 11 mounted in cutout 56 of actuator bar 50. An internally defined camming bar 64 as shown in FIG. 12 is inclined upward to a peak 65 and then downward to form two intersecting curved sides. The jaw member has a curved cutout 66 on its opposite side which fits over a curved projection 44 of the fixed jaw and a curved projection 67 which extends in cavity 46. Perspective views of the same are shown in FIGS. 11 and 12.

It can thus be seen that the intersection of the members of the assembly perform the work. The moveable jaw or inner tip is mounted to the fixed jaw member or outer tip by means of a fulcrum, and rotates on the fulcrum axis. The rotation is achieved by the relative rotation of the moveable jaw or inner tip/actuator construction, which is a distance away from the outer tip or fixed jaw fulcrum. The work performed may be as a cutter (punch) or as a grasper, both embodiments being shown. A semi-cylindrical or a conic protrusion on the inner tip or moveable jaw captures the actuator in a plane perpendicular to their axes. When using conic (dovetail) mating, the actuator may also be captured in planes parallel to the axes.

The inner tip or moveable jaw has two centers of note. One is the center or fulcrum that is mated to the actuator as described. The other is the center, or pivot, which is mated to the outer tip or fixed jaw member as described. If desired the outer shaft may be integral to the outer tip as described or separate assemblies. The outer tip or fixed jaw member is located at the end of the outer shaft furthest away from the thumb housing. The outer tip located at the end of the outer shaft is joined in such a away as to be stationary with respect to the outer shaft. This is the working end of the instrument. It will be used in conjunction with the actuator and inner tip (movable jaw) to perform a function, such a cutting (die) or grasping. Thus it can be seen that the inner tip or moveable jaw pivot has one protrusion and one recess concentric to each other. It is envisioned that they may be conic in design or cylindrical. The protrusion of the inner tip is mated with a complementary form in the outer tip, keeping the inner tip captured in one direction. The recess of the inner tip is also mated with a complementary form in the outer tip, capturing the inner tip on a radial plane. The surfaces extending radially, perpendicular to the outer tip and inner tip axes captivate the inner tip in two directions. The inner tip/ actuator relationship orbits the pivot as the actuator is moved fore and aft with respect to the pivot by moving the finger against the thumb. This inner tip/outer tip mechanism may be used a punch, scissor or grasper, or any other kind of machine.

In the foregoing description, the invention has been described with reference to a particular preferred embodiment, although it is to be understood that specific details shown are merely illustrative, and the invention may be carried out in other ways without departing from the true spirit and scope of the following claims.

What I claim is:

1. A miniature articulated tip instrument for surgical and like uses, comprising:

a thumb housing with a fixed jaw assembly mounted thereto and extending therefrom, an actuator member slidably mounted to said fixed jaw assembly, said actuator member comprising an elongated body with a distal end portion constructed with an arcuate cutout shaped to hold a complimentary shaped portion of a moveable jaw, means to drive said actuator member mounted on said thumb housing, a movable jaw defining at least one semi-cylindrical projection extending therefrom for pivotal engagement with said actuator member, said movable jaw defining and a second arcuate projection and a complimentary formed stepped cutout located on its opposite side from said second arcuate projection engaging said fixed jaw member to form a pivot point, said movable jaw member having a range of movement with respect to said fixed jaw assembly between extended and retracted positions for effecting selective user controlled pivotal working movement.

2. A miniature articulated tip instrument as claimed in claim 1 wherein said movable jaw comprises a tip housing defining a curved cutout on one side adapted to be mounted over a curved projection defined by said fixed jaw assembly and a curved projection adapted to be mounted in a curved cutout of said actuator member.

3. A miniature articulated tip instrument as claimed in claim 1 wherein said actuator member defines a slide guide which is moveably seated in a groove defined in said fixed jaw assembly.

4. A miniature articulated tip instrument as claimed in claim 1 wherein said movable jaw comprises a body with a grasping edge and defines an arcuate projection and a camming surface spaced from said arcuate projection which is inclined upwards to a peak and downward from the peak to form two intersecting curved sides.

5. A miniature articulated tip instrument as claimed in claim 1 where said fixed jaw assembly has an elongated housing which defines a throughgoing slot at its distal end portion which receives said movable jaw.

6. A miniature articulated tip instrument as claimed in claim 5 wherein said throughgoing slot has curved ends.

7. A miniature articulated tip instrument as claimed in claim 5 wherein said housing defines an arcuate projection which extends into said slot and defines a arcuate cutout which is concentric to said arcuate projection to receive a complimentary cutout and projection formed on each side of said moveable jaw assembly.

8. A miniature articulated tip instrument as claimed in claim 7 wherein said arcuate projection is frustum conical in shape.

9. A miniature articulated tip instrument as claimed in claim 1 wherein said actuator driving means is a finger housing assembly which is spring mounted to said thumb housing.

10. A miniature articulated tip instrument as claimed in claim 9 wherein said finger housing assembly defines a seat which holds the proximal end of said actuator member.

11. A miniature articulated tip instrument as claimed in claim 1 wherein said movable jaw member is provided with a serrated outer surface.

12. A miniature articulated tip instrument as claimed in claim 1 wherein said movable jaw member is provided with a blade cutting surface.

13. A miniature articulated tip instrument as claimed in claim 1 wherein said movable jaw member is provided with a grasping surface.

14. A surgical instrument comprising a first stationary jaw member, a second movable jaw member and a coupling actuator member that is movable relative to said first stationary jaw member and engages said moveable jaw member;

(a) said stationary jaw member defining at least one groove, said coupling actuator member defining a guide being slidably disposed in said at least one groove to allow axial movement along said at least one groove, said movable jaw member being mounted in a throughgoing slot defined in said first stationary jaw member and being capable of pivotal movement towards and away from said first stationary jaw member, said first stationary jaw member defining at least one arcuate projection which is mounted in a respective arcuate cutout of said moveable jaw member and an arcuate cutout which receives an arcuate projection of said movable jaw member to form a pivot point;

(b) said movable jaw member and said coupling actuator member being movably interconnected, said coupling member defining an arcuate cutout which receives an arcuate projection extending from said moveable jaw member body so as to couple said coupling member to said movable jaw member rotating said moveable jaw member relative to said first stationary jaw member; said movable jaw member further defining a stepped open arcuate cutout on one side and a complimentary stepped arcuate projection on its other side and a spaced camming surface which is inclined upwards to a peak and downward to form two intersecting curved sides.

(c) whereby when said coupling actuator member is moved in a first direction relative to said first stationary jaw member, said second movable jaw member will open away from said first stationary jaw member and when said actuator coupling member is moved in a second opposite direction relative to said first stationary jaw member, said second movable jaw member will close towards said first stationary jaw member, said first and second jaw members being arranged so that body tissue located between said first and second jaw member may be severed in a punching motion as said jaw members are opened and closed relative to one another by movement of said coupling member relative to said first stationary jaw member.

15. A surgical instrument as claimed in claim 14 wherein said coupling actuator member comprises an elongated body with a distal end portion constructed with an arcuate cutout forming an arcuate wall and a stepped arcuate cutout.

16. A surgical instrument as claimed in claim 14 where said fixed jaw assembly has an elongated housing which defines a throughgoing slot at its distal end portion, an arcuate projection extending into said slot and an opposing arcuate chamber which is adapted to receive an arcuate projection of said movable jaw.

17. A miniature articulated tip instrument assembly comprising:

(a) a fixed jaw housing with an elongated member extending therefrom, said elongated member defining a channel therein and having a distal end portion provided with a throughgoing slot and a pivotal mounting integrally formed therein for a movable jaw member;

(b) an elongated drive member moveably mounted on said elongated member with its distal end being provided with at least one movable jaw member connecting means;

(c) means to drive said elongated drive member mounted to said fixed jaw housing;

(d) a movable jaw member mounted for rotation on said pivotal mounting of said fixed housing, said movable jaw member defining a semi-cylindrical projection which is mounted in a semi cylindrical cutout of said elongated drive member and an arcuate projection with a transverse sidewall which is positioned into a similarly shaped cutout cut through a wall of said movable jaw member into said throughgoing slot, said movable jaw member further defining a cutout positioned opposite said arcuate projection which is positioned over an arcuate projection extending from said fixed jaw housing into said throughgoing slot for rotating said jaw member towards or away from said fixed jaw housing elongated member to provide selective grasping, clamping, or cutting action.

* * * * *